US006251863B1

(12) United States Patent
Yue

(10) Patent No.: US 6,251,863 B1
(45) Date of Patent: Jun. 26, 2001

(54) METHOD OF PREVENTING AND TREATING SYMPTOMS OF AGING AND NEURODEGENERATIVE DYSFUNCTIONS WITH RELAXIN

(76) Inventor: Samuel K. Yue, 4928 Poppy La., Edina, MN (US) 55435

( * ) Notice: Subject to any disclaimer, the term of this patent is extended or adjusted under 35 U.S.C. 154(b) by 0 days.

(21) Appl. No.: 09/252,339

(22) Filed: Feb. 18, 1999

Related U.S. Application Data
(60) Provisional application No. 60/099,403, filed on Sep. 8, 1998.
(51) Int. Cl.[7] .......................... A61K 38/00; A01N 37/18; C07K 5/00; C07K 7/00
(52) U.S. Cl. .................................. 514/12; 514/2; 530/324
(58) Field of Search ............................ 514/12.2; 536/324

(56) References Cited

U.S. PATENT DOCUMENTS

| 4,267,101 | 5/1981 | Bigazzi . |
| 4,624,804 | 11/1986 | Voelter et al. . |
| 4,656,249 | 4/1987 | Tregear et al. . |
| 4,835,251 | 5/1989 | Burnier et al. . |
| 5,089,419 | 2/1992 | Kuniyuki . |
| 5,108,897 | 4/1992 | Steinetz et al. . |
| 5,145,962 | 9/1992 | Hudson et al. . |
| 5,166,191 | 11/1992 | Cronin et al. . |
| 5,179,195 | 1/1993 | Hudson et al. . |
| 5,223,408 | 6/1993 | Goeddel et al. . |
| 5,279,942 | 1/1994 | Kuniyuki . |
| 5,320,953 | 6/1994 | Hudson et al. . |
| 5,326,694 | 7/1994 | Hudson et al. . |
| 5,451,572 | 9/1995 | Cipolla et al. . |
| 5,464,756 | 11/1995 | Henner et al. . |
| 5,478,807 | 12/1995 | Cronin et al. . |
| 5,612,051 | 3/1997 | Yue . |
| 5,656,592 | 8/1997 | Seed et al. . |
| 5,753,623 | 5/1998 | Amento et al. . |
| 5,759,807 | 6/1998 | Breece et al. . |
| 5,811,388 | 9/1998 | Friend et al. . |
| 5,811,395 | 9/1998 | Schwabe et al. . |

OTHER PUBLICATIONS

Guller, S., et al., "Negative Regulation of Placental Fibronectin Expression by Glucocorticoids and Cyclic Adenosine 3', 5'-Monophosphate$^{a,b}$," Annals New York Academy of Sciences, 734:132–142, (1994).

MacLennan, A.H., et al., "Ripening of the Human Cervix and Induction of Labor With Intracervial Purified Porcine Relaxin," Obstetrics & Gynecology, 68(5):598–601, (1986).

Poisner, A.M., et al., "Relaxin Stiumulates the Synthesis and Release of Prorenin from Human Decidual Cells: Evidence for Autocrine/Paracrine Regulation," Journal of Clinical Endocrinology and Metabolism, 70:(6):1765–1767, (1990).

Büllesbach, E.E., et al., "Total Synthesis of Human Relaxin and Human Relaxin Derivatives by Solid–phase Peptide Synthesis and Site–directed Chain Combination," The Journal of Biological Chemistry, 266(17):10754–10761, (1991).

O'Day–Bowman, M.B., et al., "Hormonal Control of the Cervix in Pregnant Gilts. III. Relaxin's Influence on Cervical Biochemical Properties in Ovariectomized Hormone–Treated Pregnant Gilts," Endocrinology, 129(4): 1967–1976, (1991).

Saugstad, L.F., "Persistent Pelvic Pain and Pelvic Joint Instability," European Journal of Obstetrics & Gynecology and Reproductive Biology, 41:197–201, (1991).

Büllesbach, E.E., et al., "The Receptor–binding Site of Human Relaxin II," The Journal of Biological Chemistry, 267(32):22957–22960, (1992).

Hall, J.A., et al., "Influence of Ovarian Steroids on Relaxin–Induced Uterine Growth in Ovariectomized Gilts," Endocrinology, 130(6):3159–3166, (1992).

Kibblewhite, D., et al., "The Effect of Relaxin on Tissue Expansion," Arch Otolaryngol Head Neck Surgery, 118:153–156, (1992).

Lee, A.B., et al., "Monoclonal Antibodies Specific for Rat Relaxin. VI. Passive Immunization with Monoclonal Antibodies throughout the Second Half of Pregnancy Disrupts Histological Changes Associated with Cervical Softening at Parturition in Rats," Endocrinology, 130(4):2386–2391, (1992).

Bell, R.J., et al., "A Randomized, Double–Blind, Placebo–Controlled Trial of the Safety of Vaginal Recombinant Human Relaxin for Cervical Ripening," Obstetrics & Gynecology, 82(3):328–333, (1993).

Bryant–Greenwood, G.D., et al., "Sequential Appearance of Relaxin, Prolactin and IGFBP–1 During Growth and Differentiation of the Human Endometrium," Molecular and Cellular Endocrinology, 95:23–29, (1993).

Chen, S.A., et al., "The Pharmacokinetics of Recombinant Human Relaxin in Nonpregnant Women After Intravenous, Intravaginal, and Intracervical Administration," Pharmaceutical Research, 10(6):834–838, (1993).

Huang, C., et al., "Stimulation of Collagen Secretion by Relaxin and Effect of Oestrogen on Relaxin Binding in Uterine Cervical Cells of Pigs," Journal of Reproduction and Fertility, 98;153–158, (1993).

(List continued on next page.)

Primary Examiner—Avis M. Davenport
(74) Attorney, Agent, or Firm—Fredrikson & Byron, P.A.

(57) ABSTRACT

A method of treating neurodegenerative dysfunctions and aging symptoms includes administering a therapeutically effective amount of relaxin to a patient. Neurodegenerative dysfunctions amenable to treatment with relaxin include Alzheimer's, attention deficit disorder, Parkinson's, and others.

2 Claims, No Drawings

OTHER PUBLICATIONS

Osheroff, P.L., et al., "Expression of Relaxin mRNA and Relaxin Receptors in Postnatal and Adult Rat Brains and Hearts," The Journal of Biological Chemistry, 268(20):15193–15199, (1993).

Saxena, P.R., et al., "Is the Relaxin System a Target for Drug Development? Cardiac Effects of Relaxin," TiPS, 14:231, (1993).

Weiss, G., et al., "Elevated First–Trimester Serum Relaxin Concentrations in Pregnant Women Following Ovarian Stimulation Predict Prematurity Risk and Preterm Delivery," Obstetrics & Gynecology, 82(5):821–828, (1993).

Winn, R.J., et al., "Hormonal Control of the Cervix in Pregnant Gilts. IV. Relaxin Promotes Changes in the Histological Characteristics of the Cervix That Are Associated with Cervical Softening During Late Pregnancy in Gilts," Endocrinology, 133(1):121–128, (1993).

Büllesbach, E.E., et al., "Functional Importance of the A Chain Loop in Relaxin and Insulin," The Journal of Biological Chemistry, 269(18):13124–13128, (1994).

Critchley, H.O.D., et al., "Is Ovarian Relaxin a Stiumulus to Placental Protein 14 Secretion in Pregnancy?," Journal of Endocrinology, 142:375–378, (1994).

Colon, J.M., et al., "Relaxin Secretion into Human Semen Is Independent of Gonadotropin Stimulation," Biology of Reproduction, 50:187–192, (1994).

Evans, B.A., et al., "Characterization of Two Relaxin Genes in the Chimpanzee," Journal of Endocrinology, 140:385–392, (1994).

Golub, M.S., et al., "Effect of Short–Term Infusion of Recombinant Human Relaxin on Blood Pressure in the Late–Pregnant Rhesus Macaque (*Macaca mulatta*)," Obstetrics & Gynecology, 83(1):85–88, (1994).

Jauniaux, E., et al., "The Role of Relaxin in the Development of the Uteroplacental Circulation in Early Pregnancy," Obstetrics & Gynecology, 84(3):338–342, (1994).

Johnson, M.R., et al., "The Regulation of Plasma Relaxin Levels During Human Pregnancy," Journal of Endocrinology, 142:261–265, (1994).

Lane, B., et al., "Decidualization of Human Endometrial Stromal Cellsin vitro:Effects of Progestin and Relaxin on the Ultrastructure and Production of Decidual Secretory Proteins," Human Reproduction, 9(2):259–266, (1994).

Lanzafame, F., et al., "Pharmacological Stimulation of Sperm Motility," Human Reproduction, 9(2):192–199, (1994).

Petersen, L.K., et al., "Normal Serum Relaxin in Women with Disabling Pelvic Pain during Pregnancy," Gynecol Obstet Invest, 38:21–23, (1994).

Stemmermann, G.N., et al., "Immunocytochemical Identification of a Relaxin–like Protein in Gastrointestinal Epithelium and Carcinoma: a Preliminary Report," Journal of Endocrinology, Ltd., 140:321–325, (1994).

Tashima, L.S., et al., "Human Relaxins in Normal, Benign and Neoplastic Breast Tissue," Journal of Molecular Endocrinology, 12:351–364, (1994).

Winn, R.J., et al., "Individual and Combined Effects of Relaxin, Estrogen, and Progesterone in Ovariectomized Gilts. I. Effects on the Growth, Softening, and Histological Properties of the Cervix," Endocrinology, 135(3):1241–1249, (1994).

Winn, R.J., et al., "Individual and Combined Effects of Relaxin, Estrogen, and Progesterone in Ovariectomized Gilts. II. Effects on Mammary Development," Endocrinology, 135(3):1250–1255, (1994).

Bryant–Greenwood, G.D., et al., "Human Relaxins: Chemistry and Biology," Endocrine Reviews, 15(1):5–26, (1994).

Johnson, M.R., et al., "Relationship Between Ovarian Seroids, Gonadotrophins and Relaxin During the Menstrual Cycle," Acta Endocrinologica, 129;121–125, (1993).

Henriksson, K.G., "Pathogenesis of Fibromyalgia," Review Articles–Myofascial Pain Syndromes and Fibromyalgia, Journal of Musculoskeletal Pain, 1(3/4):3–16, (1993).

Masi, A.T., "Review of the Epidemiology and Criteria of Fibromyalgia and Myofaxcial Pain Syndromes: Concepts of Illness in Populations as Applied to Dysfunctional Syndromes," Epidemiology and Natural History–Myofaxcial Pain and Fibromyalgia, Journal of Musculoskeletal Pain, 1(3/4):113–136, (1993).

Posner, I.A., "Treatement of Fibromyalgia Syndrome with Intravenous Lidocaine: A Prospective, Randomized Pilot Study," Journal of Musculoskeletal Pain, 2(4):55–65, (1994).

Bennett, R.M., "Fibromyalgia Review," Literature Reviews, Journal of Musculoskeletal Pain, 2(4):99–112, (1994).

"Foreword: NIH Conference on Fibromyalgia," Journal of Musculoskeletal Pain, 2(3): p. xiii–xv (1994).

Yunnus, M.B., "Fibromyalgia Syndrome: Clinical Features and Spectrum," Journal of Musculoskeletal Pain, 2(3):5–21, (1994).

Wolfe, F., "Fibromyalgia: On Criteria and Classification," Journal of Musculoskeletal Pain, 2(3):23–39, (1994).

Wolfe, F., "Aspects of the Epidemiology of Fibromyalgia," Journal of Musculoskeletal Pain, 2(3):65–77, (1994).

Russell, I.J., "Biochemical Abnormalities in Fibromyalgia Syndrome," Journal of Musculoskeletal Pain, 2(3):101–113, (1994).

Goldenberg, D.L., "Medications/Clinical Trials in Fibromyalgia," Therapeutic Interventions, Journal of Musculoskeletal Pain, 2(3):135–141, (1994).

Wolfe, F.,"When to Diagnose Fibromyalgia," Diagnostic Issues, Rheumatic Disease Clinics of North America, 20(2): 485–501, (1994).

Rothschild, B., et al., "Retrospective Assessment of Fibromyalgia Therapeusis," Comprehensive Therapy, 20(10:545–549, (1994).

Wolfe, F., "Post–traumatic Fibromyalgia: A Case Report Narrated by the Patient," Arthritis Care and Research, 7(3):161–165, (1994).

"Testimony to the U.S. Senate Appropriations Subcommittee on Labor, Health & Human Services, and Education," [and attachments], (1995).

METHOD OF PREVENTING AND TREATING SYMPTOMS OF AGING AND NEURODEGENERATIVE DYSFUNCTIONS WITH RELAXIN

CROSS REFERENCE TO RELATED APPLICATIONS

This application claims priority from provisional application Ser. No. 60/099,403, filed Sep. 8, 1998.

BACKGROUND OF THE INVENTION

The present invention relates to symptoms associated with aging and/or neurodegenerative dysfunctions and their treatment with relaxin.

No one can avoid aging and the effects it has on our ability to think, act and feel. Many prominent conditions are associated with aging including lack of mobility and flexibility, osteoporosis, loss of skin elasticity, respiratory distress, muscle loss, memory loss, cognitive and affective impairment, osteodegenerative impairment of the joints, and cardiac failures, etc. In addition to impairment of many body functions associated with normal aging, some people develop advanced forms of these dysfunctions. For example, Alzheimer's disease and Parkinson's disease commonly afflict the elderly population.

An estimated four million Americans have Alzheimer's disease. The disease primarily affects those over 65 years of age, particularly over age 85. Women also have a greater risk of developing Alzheimer's. While there is no cure for Alzheimer's disease, the list of potential agents to treat its symptoms keep growing. For example, current attempts at treatment include cholinesterase inhibitors, ginkgo, acetyl-L-carnitine, ampakines, calcium channel blockers, antioxidants, and nerve growth factors, among others.

Parkinson's disease is another debilitating malady affecting a large segment of the elderly population. Parkinson's disease is commonly characterized by rigidity of the musculature, tremors at rest, and a serious inability to initiate movement. These symptoms are likely caused by a loss of dopamine secretion and destruction of the substantia nigra, which permits hyperactivity of the acetylcholine pathways.

Given the already large elderly population, and its sure, booming growth in the United States in the next thirty years, treatments that either cure or substantially reduce the symptoms of these widespread diseases and normal aspects of aging will become quite valuable. These treatments will enable a greater segment of the population to remain active without assistance and will reduce the staggering cost of nursing and health care for these patients.

SUMMARY OF THE INVENTION

The present invention is based on the recognition that some of the symptoms associated with aging and/or neurodegenerative dysfunctions (such as memory loss, poor cognitive function, negative behavioral patterns, and sleep disturbance) can be alleviated by relaxin, and may in fact be caused by a decrease of relaxin in the bloodstream. This lack of relaxin in the blood stream may be congenital or the result of another mechanism which suppresses the normal production or action of relaxin. In addition, relaxin stimulates and/or modulates other hormones, proteins, and vital body fluids, which all affect these symptoms. Accordingly, a method of the present invention of treating symptoms associated with aging and/or neurodegenerative disease and dysfunctions comprises administering to a patient exhibiting symptoms associated with these conditions a therapeutically effective amount of relaxin.

This recognition is based on clinical observations by the inventor of the symptoms reported by patients with fibromyalgia syndrome (FMS) when these patients take relaxin. In particular, the basic observation is that fibromyalgia patients no longer report or exhibit the same symptoms (e.g., poor memory, poor cognition, sleep disturbance, and poor behavior) when they are receiving relaxin that they report and/or exhibit without taking relaxin. In short, many or all of the symptoms associated with these conditions diminish or disappear when these patients are receiving relaxin therapy.

Many of these signs and symptoms affecting FMS patients are also symptoms affecting patients that have aged or that have Alzheimer's, Parkinson's, and/or other conditions such as ADD. Accordingly, to the extent that relaxin alleviates these symptoms in FMS patients, relaxin will alleviate the same symptoms in naturally aging patients and/or in Alzheimer's, Parkinson's, and ADD patients. This relationship primarily stems from the way that relaxin acts on different parts and pathways of the body, most notably the brain. Of course, many of these symptoms treatable with relaxin also are associated with aging, whether the symptoms stem from a particular disease or not.

BRIEF DESCRIPTION OF THE DRAWINGS

This application contains no drawings.

DETAILED DESCRIPTION OF THE PREFERRED EMBODIMENTS

I. Definition of Relaxin

Relaxin has been extensively documented regarding its presently known structure, functions, and properties. See Bryant-Greenwood, et al., Human Relaxin: Chemistry and Biology, Endocrine Reviews, Vol. 15, No. 1, (1994), and the articles cited therein.

Relaxin has been well defined in its natural human form, animal form, and in its synthetic form. In particular, relaxin has been extensively described in Cronin, et al., U.S. Pat. No. 5,166,191 and Burnier, et al., U.S. Pat. No. 4,835,251, both of which are hereby incorporated by reference. In this application, "relaxin" will generally refer to the terms "relaxin," "human relaxin," "native relaxin," and "synthetic relaxin," and the terms "human relaxin" and "human relaxin analogs." "Relaxin" in this application will also refer to relaxin as isolated in pigs, rats, horses and relaxin produced by recombinant techniques based cDNA clones for rat or porcine relaxin. In addition, "relaxin" will also refer to pro relaxin, preprorelaxin, relaxin analogues, derivatives, peptides with relaxin activity, as well as other relaxin variants obtained by addition, substitution, or deletions of one or more relaxin components.

All of the various forms of relaxin identified above are defined and described in the following U.S. Patents: Cronin, et al., U.S. Pat. No. 5,166,191 USE OF RELAXIN IN CARDIOVASCULAR THERAPY; Cronin, et al., U.S. Pat. No. 5,478,807 USE OF RELAXIN IN THE TREATMENT OF BRADYCARDIA; Burnier, et al., U.S. Pat. No. 5,835,251 METHOD OF CHAIN COMBINATION; Cipolla, et al., U.S. Pat. No. 5,451,572 HUMAN RELAXIN FORMULATION; Breece, et al., U.S. Pat. No. 5,759,807 PROCESS FOR PRODUCING RELAXIN; Hudson, et al., U.S. Pat. Nos. 5,320,953 and 5,326,694 PROCESS FOR SYNTHESIZING HUMAN H2-PRORELAXIN, HUMAN H2-RELAXIN, AND FUSION PROTEINS THEREOF;

Hudson, et al., U.S. Pat. No. 5,179,195 HUMAN RELAXIN POLYPEPTIDES; Hudson, et al., U.S. Pat. No. 5,145,962 HUMAN PRO RELAXIN POLYPEPTIDES; Tregear, et al., U.S. Pat. No. 4,656,249 PEPTIDES WITH RELAXIN ACTIVITY; Voelter, et al., U.S. Pat. No. 4,624,804 PROCESS OF PREPARING RELAXIN FROM MILK; and Schwabe, et al., U.S. Pat. No. 5,811,395 RELAXIN ANALOGS AND DERIVATIVES METHODS AND USES THEREOF, all of which are hereby incorporated by reference.

Other methods of making relaxin and its analogs, and methods for isolating and purifying relaxin, are known in the art. In addition to the above-cited patents, several sources for these methods are identified in U.S. Pat. No. 5,166,191 including the following references:, Barany et al., The Peptides 2, 1 (1980); Treager et al., Biology of Relaxin and its Role in the Human, pp. 42–55; EP 251,615; EP 107,782; EP 107,045; and WO 90/13659.

All variations of relaxin described above fall within the scope of the invention provided that the primary physiologic and biologic functional activity of relaxin is maintained.

II. Prevention and Treatment of Symptoms of Anti-Aging, and/or Neurodegenerative Dysfunctions Including Alzheimer's Disease, Parkinson's Disease, and Attention Deficit Disorder A. Relaxin as an Anti-Aging Treatment 1. General Relationship between Symptoms of Fibromyalgia and Symptoms of Aging, and their Treatment with Relaxin Fibromyalgia patients appear to age significantly faster than the general population. The basic characteristics of fibromyalgia patients are described in Yue, U.S. Pat. No. 5,612,051, METHOD OF TREATING INVOLUNTARY MUSCLE DYSFUNCTION WITH RELAXIN HORMONE. Fibromyalgia patients often times have memory loss, sleep disturbance and cognitive dysfunction and affective dysfunction. These fibromyalgia patients frequently mimic symptoms shown by the elderly population of the ages of late 70s through age 90 and beyond. This type of central nervous system dysfunction occurs much earlier in fibromyalgia patients (who are in their 30s and 40s), together with pain, muscle tightness and weakness, fatigue and various problems associated with this disease. These problems frequently include irritable or spasm bowel, osteodegenerative and osteoporotic changes of the spine, dysautomonia (dysfunction and poor control of internal organs), and others. Many late manifestations of the dysautomonia and other age-related changes in one's body, e.g., bladder control, swallowing difficulty, circulation, bony changes, etc. in the elderly population also occur rather early in the fibromyalgia population. Osteodegenerative and osteoporotic changes of the spine are extremely prevalent in the fibromyalgia population. Fibromyalgia patients appear to age much earlier and faster than the general population. Degradation of the connective tissue occurs prematurely. Growth of the skin, hair and nails is retarded, while wound-healing and immuno-response to infections, stress and injuries are blunted. Other premature aging symptoms include dyspepsia or GI tract problems, control of hollow organs and its sphincters, chemical sensitivities, hypoglycemia, and others. All of these findings reflect premature aging of the body parts and functions resulting in premature derangement of the internal and external environments or milieu of the fibromyalgia patient.

As supported by the inventor's current clinical observations, relaxin supplements given to the fibromyalgia patients restores most of these premature-aging symptoms and problems. Accordingly, relaxin functions as an essential hormone within a normal person's body to prevent premature aging of his/her body parts and functions. If a deficit of relaxin leads to fibromyalgia and premature aging, then age-related decline of relaxin likely explains the normal aging of one's body parts and functions. Since many of the aging symptoms and problems are similar in the fibromyalgia and elderly populations, a deficit of relaxin early in one's life leads to fibromyalgia and its related premature aging difficulties, and age-related decline of relaxin leads to normal aging difficulties in the elderly population.

Genetically-blessed individuals with healthy genes who live a long, healthy life may be related to abundant production of relaxin throughout their life. Taking a relaxin supplement will be an artificial way of improving a person's health status and mimicking these genetically-blessed individuals.

Therefore, relaxin supplements given to the elderly can prevent premature aging of internal organs, skin, joints and other body parts and functions. The elderly can be kept healthy with relaxin supplements until some organs break down according to their internal clock or predetermined life span. Slow, degenerative, and vegetative death may be avoided.

2. Treatment of Skin and General Appearance with Relaxin

Relaxin's effect on connective tissues during late pregnancy has been well-documented. Relaxin improves the integrity of the connective tissues, maintains the elasticity and circulation of the skin, sustains the youthful and radiant appearance of the face, increases hair and nail growth, and stimulates other changes during pregnancy.

However, middle-aged fibromyalgia patients given oral relaxin supplements also report similar changes with their connective tissues. They also report changes identical to those observed during a pregnancy (which correlates with high levels of serum relaxin), such as return of elasticity and circulation of the skin, youthful and radiant appearance of their faces, and increased hair and nail growth, and other pregnancy-type changes. Therefore, minute doses of oral relaxin will be given to middle-aged, well populations to improve their overall complexion, maintain youthfulness, prevent premature aging of connective tissues surrounding the external body. This relaxin supplement will also maintain optimal functioning of the internal organs within the individual's internal body environment. Relaxin also will be applied topically through ultrasound and gel, transdermal delivery systems, and other topical means to solely affect the elasticity of the skin to prevent premature aging of the facial, body, neck, breast, and buttock skin. When a person receives adequate amounts of relaxin, relaxin causes collagen to fill in between and within the cells of the connective tissues underneath the skin, keeps the skin taut secondary to elasticity, and thereby eliminates or minimizes the appearance of cellulite.

3. Treatment of Osteodegenerative Changes of the Joints with Relaxin

Osteodegenerative changes of the joints of one's body are commonly associated with tight muscles, ligaments and tendons. Rapid wear and tear of the joints, from the shearing forces generated by these tight muscles, ligaments and tendons, leads to many of the commonly-observed early degenerative joint diseases found within one's skeletal system. Many expensive medical interventions are necessary to alleviate pain and suffering and to restore daily functions on these otherwise healthy people. These interventions include joint debridement and replacements, back surgery and other surgeries, diagnostic and therapeutic injections, rehabilitation, physician appointments, laboratory work-ups, radiographic work-ups, hospital stays, etc.

Fibromyalgia patients are known to have tight muscles, ligaments, and tendons. They also exhibit early signs of osteodegenerative changes of their joints at a very young age. Further, fibromyalgia patients as a whole undergo more corrective surgeries than the normal population. Fibromyalgia patients who receive relaxin supplements report a significant decrease of muscle tightness, increased range of motion in their joints, and decreased stiffness of the ligaments and tendons surrounding the joints. The increased flexibility of the joints reduces the exerted shearing forces generated from the muscles, ligaments and tendons, thereby reducing or arresting the osteodegenerative changes of the joints. Therefore, relaxin supplements will be given to these individuals who suffer congenitally (probably secondary to borderline deficit of relaxin) from tight muscles, ligaments and tendons to restore the flexibility of the joints and eliminate or arrest the osteodegenerative disease of the joints.

Premature osteodegenerative changes on the joints of normal people can be treated with relaxin and glucosamine sulfate. Glucosamine sulfate has been shown to improve joint cartilage breakdown on an otherwise normal person (i.e., not a FMS patient) who suffers from osteodegenerative joint disease. It is preferable treatment for the inflammation and pain of the joints instead of nonsteroidal anti-inflammatory drugs (NSAIDS) which is the present recommended treatment of choice. Cartilage consists of collagen, proteoglycans, chondrocytes and a large amount of water. One's body supply of proteoglycan and collagen within the cartilage is governed by the health of the chondrocytes. A balanced dynamic process between degeneration and regeneration of the collagen and proteoglycan by the chondrocytes maintains the health of the cartilage. Proteogylcan, a water loving molecule, holds and strings the collagen together in a matrix and imparts shape, size, and resiliency to the cartilage. Chondrocytes are found within this matrix and are the sole producers of the collagen and proteoglycan. In the early stage of osteodegeneration or osteoarthritis of the joints, the cartilage appears unable to resist the shearing force exerted on the joints and therefore releases proteogylcan into the synovial fluid of the joints. Fibrillation of the fibrous collagen matrix also releases fibrils into the synovial fluid. Without the protection of this matrix, chondrocytes are easily damaged with progressive stress that eventually leads to tissue death. As the disease progress, bits of cartilage debris shear off the cartilage surface and accumulate on the synovium of the joints resulting in pain and irritation of the joints. A body immunity response is then activated, in which mast cells are deposited on the synovium, and an inflammation process is activated through the release of prostaglandin into the synovium tissue. Collagenase and proteoglycanase are then secreted into the joints causing further and faster breakdown of the cartilage. The end result of this accelerated process is the total destruction of the cartilage and later the joints.

Glucosamine sulfate has been demonstrated to inhibit collagenase and also phospholipase A2, an activator of collagenase, resulting in complete suppression of collagenase activity. Fibromyalgia patients with osteoarthritis treated with glucosamine sulfate do not seem to respond as readily as normal population who suffer from the same disease. However, fibromyalgia patients with osteoarthritis treated with both relaxin and glucosamine sulfate responded favorably—even faster than the general population with the same osteoarthritis. Therefore, the production of the collagen by the chondrocytes is facilitated by relaxin. Good quality collagen is produced in the presence of relaxin, which binds with proteogylcan to form strong resilient cartilage. Together with the deactivation of the collagenase by the glucosamine sulfate, homeostasis of the cartilage regeneration and degeneration are maintained and the joint is returned to its formal healthy state. Accordingly, relaxin enhances the effect of glucosamine sulfate in retarding and restoring osteodegenerative changes of the joints.

4. Treatment of Osteoporosis with Relaxin

Osteoporosis begins early, particularly in women. The most significant change of osteoporosis in women occurs during menopause. During and after menopause, in spite of hormonal replacement, increased intake of calcium, adequate amounts of weight-bearing exercises, and medications to slow the re-absorption of calcium from the bony matrix, osteoporosis continues relentlessly. Adequate prevention and available medical treatments only blunt the progression of osteoporosis. Lack of prevention and inadequate medical treatment leads to rapid progression of the disease, particularly in susceptible persons. Thus far, osteoporosis appears to be an inevitable disease that is irreversible. One of the often-mentioned major factors in osteoporosis is the age-related degradation of collagen within the bony matrix. Good quality collagen within the bony matrix serves as a good foundation to hold the calcium in place allowing for strong bone formation. This foundation is analogous to good cement (strong collagen within bony matrix) that holds the iron rod (calcium) within its fold to form strong concrete (bone).

Pathology on the production of collagen within the bony matrix results in a congenital disease known as osteogenesis imperfecta or "brittle bony disease." These unfortunate patients suffer from fractures of their bones from the tiniest amount of trauma to their body. Even slight movement of their body may result in fractures. Advanced cases of fibromyalgia with severe osteoporosis also exhibit a similar tendency to fractures from any movement of their body. The radiographic examination of these two diverse types of patients with similar collagen degradation pathology reveals some striking similarity. Both sets of patients show diffuse osteoporotic changes of their bones that are prone to fracture.

Age-related degradation of collagen within one's body is directly related to age-related decline of relaxin. Therefore, age-related degradation of collagen within the bony matrix also must be related to age-related decline of relaxin. Replacing the relaxin lost in this age-related decline of relaxin will arrest and may reverse the age-related progression of osteoporosis. Fibromyalgia patients are notoriously known to have rapid progression of osteoporosis at a much younger age than the normal population. Fibromyalgia patients are also known to be deficient of relaxin at a much younger age than the normal population. While insufficient time has elapsed on those fibromyalgia patients taking relaxin supplements to document the reversibility or arrest of their osteoporosis, relaxin will likely arrest and may reverse the disease because of its action on the collagen within the bony matrix. Therefore, giving relaxin during early stages to persons susceptible to osteoporosis will likely prevent premature progression of the disease. Relaxin also can be given to persons with severe forms of osteoporosis or with "brittle bone disease" to arrest the progression of their disease and minimize their pain and suffering from frequent fractures.

5. Preventive Treatment of Cardiac Function with Relaxin

Relaxin has a protective effect on the cardiac muscles of the studied animals (both in vivo and in vitro). Numerous receptor sites are found in the cardiac system. In addition, the nitric oxide pathway (established by Nobel prize winners Forchgott, Ignarro, and Murad) is activated by relaxin which relaxes all smooth muscles and particularly the smooth muscles of coronary arteries, thus protecting the heart and other areas. Relaxin, therefore, imparts a protective effect on the cardiac system. Relaxin also affects the chronotropic and inotropic action of the heart and, therefore, the pumping mechanism. Relaxin's relaxation effect on the smooth muscles within the blood vessels prevents sudden ischemia of the heart from vasospasm of the coronary arteries. Sudden arrhythmia, which is common in the fibromyalgia population and elderly population, may be a result of a deficit of relaxin. Adequate relaxin supplements given to the elderly and fibromyalgia patients may prevent arrhythmia of the heart, ischemia from vasospasm, early cardiac pumping failure, and other cardiac abnormality. Early preventive use of relaxin supplements on persons with strong familial history of cardiac disease may prevent the development of cardiac disease at a relatively young age.

6. Prevention of Muscle Loss with Relaxin

With respect to anti-aging, experimental gene therapy includes administration of growth hormone (GH) and peripheral insulin-like growth factors (IGF) to promote muscle gain. For example, this type of gene therapy was reported in 1998 at the annual meeting of the American Society for Cell Biology in San Francisco, Calif. by University of Pennsylvania Medical School in Philadelphia (published in the Proceedings of the National Academy of Sciences).

However, relaxin stimulates and modulates GH and peripheral IGF that are already present in the bloodstream. Accordingly, administering relaxin alone to a patient will cause relaxin to act on GH and IGF in the bloodstream, stimulating and modulating them, to reverse age-related muscle atrophy and eliminate the need for this type of gene therapy. For example, relaxin and muscle growing hormones or factors may be coupled with fibrinogen or other biodegradable polymer and injected into the muscles. Relaxin and other hormones would then slowly release into the surrounding muscles to mimic the effect of the gene therapy.

7. Conclusion

Relaxin, therefore, appears to be a regulator and modulator of our internal and external body system as a whole. A small, adequate amount of relaxin within our body is necessary for health preservation and to maintain healthy milieu of our body. Many degenerative and metabolic diseases of our body may be directly and indirectly related to the deficit of this hormone. Oral supplements to replace relaxin deficit may prevent the premature development of many of these age-related degenerative and metabolic diseases.

B. Relaxin as a Preventor and Treatment for Alzheimer's Disease

In addition, to the anti-aging symptoms treatable with relaxin described above, relaxin can be used to treat other age-related neurodegenerative dysfunctions such as Alzheimer's disease. At least three elements of fibromyalgia syndrome (FMS) and Alzheimer's disease are quite similar: sleep disturbance, cognitive dysfunction and affective dysfunction. As described in Yue, U.S. Pat. No. 5,612,051, METHOD OF TREATING INVOLUNTARY MUSCLE DYSFUNCTION WITH RELAXIN, and as confirmed by continuing clinical treatment and observations, relaxin prevents and reverses the signs and symptoms of FMS including symptoms of sleep disturbance, and cognitive, affective and behavior dysfunction. Since the signs and symptoms of Alzheimer's are quite similar to those of FMS, relaxin will likely relieve those symptoms in Alzheimer's patients.

Examination of this problem includes knowledge of the triad of affective, behavior and cognitive aspects of the central nervous system (CNS) wherein the cognitive and affective dysfunction of the CNS changes the behavior function of the patient. Memory recall and concentration components of the cognitive dysfunction appears to be helped by relaxin. For example, fibromyalgia patients treated with relaxin have been observed with noticeable improvements in affective, behavior, and cognitive functions such as increased short term memory, heightened task orientation, as well as more socially positive affective responses with accompanying positive behavior displays (e.g., emotionally calm).

Relaxin supplements have been shown to restore the cognitive, affective, and sleep dysfunction within the central nervous system suffered by the fibromyalgia patients. Elderly persons who suffer from Alzheimer's disease also exhibit similar cognitive, affective and sleep dysfunction within the central nervous system. This is postulated to be secondary to neurodegenerative changes within the forebrain in the area dealing with short-term memory and other functions. These areas of the forebrain are supplied with abundant receptor sites for relaxin, in addition to other areas. Therefore, relaxin will play a role in preventing the neurodegenerative changes within the central nervous system. Short-term memory loss, irritability, sleep disturbances, behavior changes, and other symptoms related to Alzheimer's disease will be prevented or arrested by relaxin supplementation. Further, the integrity of any functions of the central nervous system as a whole will be maintained in the optimal state by relaxin supplementation until the demise of the individual.

Estrogen therapy in women is known to help prevent and treat Alzheimer's in women. In one aspect, estrogen helps to maintain the integrity of the hippocampus, which is part of the limbic system of the brain, and is believed to be involved in memory. Accordingly, combining relaxin with estrogen therapy will further improve the memory function of an Alzheimer's patient.

Moreover, the hippocampus region of the brain has been recently discovered to exhibit regeneration of nerve endings related to Alzheimer's disease. This phenomenon refutes the long held notion that nerve cells within the brain are static and that the once the nerve cells die, no regeneration can occur. In addition, oxidative stress process (a process of inflammation) is also found to be much higher in this same region of the brain in Alzheimer's disease. These two processes imply that the dynamic regeneration and degeneration of the nerve cells are not in balance resulting in faster degeneration than regeneration. This area of hippocampus is also known to have abundant relaxin receptor sites. Therefore, it is likely that a deficit of relaxin impedes the regeneration of nerve cells, and hastens the destructive oxidative process resulting in more nerve cell degeneration. Administering relaxin to these patients will correct this imbalance, thereby preventing and minimizing neurodegenerative diseases, such as Alzheimer's disease.

C. Relaxin as Preventor and Treatment of Parkinson's Disease

In addition, Parkinson's patients exhibit signs and symptoms similar to advanced FMS patients, such as tremors, stiffness, pain from contracted muscles, incoordination, and many CNS symptoms. The inventor has treated many FMS patients with these signs and symptoms which improve with relaxin and therefore a similar improvement will be seen in Parkinson's patients. The inventor believes that relaxin plays a role in producing and/or regulating dopamine. Once the mechanism of dopamine production is halted, it will regain its ability slowly but never completely. Therefore, administering relaxin at early stages of Parkinson's will solve early stages of Parkinson's and prevent its progression.

D. Treatment of Attention Deficit Disorder with Relaxin

Attention Deficit Disorder (ADD) without the hyperactivity component is believed to also be related to a deficit of relaxin. Relaxin appears to affect selection of information into the brain and the decision to store it in long term memory or to discard the information. This activity is believed to occur at the hippocampus, which is a known site for relaxin receptors. The inventor believes that ADD manifests itself in this area of the brain based on clinical observations of patients with apparent ADD. In particular, some patients with FMS appear to have ADD. For example, one patient presented with a family history of ADD and of pain over their entire body (a core FMS symptom). The inventor believes that this type of patient's apparent ADD is actually a central nervous system (CNS) manifestation of FMS. Other specialists observing the ADD-like symptoms ignore the pain symptoms of FMS. Accordingly, since many patients with FMS find relief from the signs and symptoms of their CNS dysfunctions with relaxin, which are closely related to signs and symptoms of ADD, then patients with only signs and symptoms of ADD will have their symptoms treated and reversed with relaxin.

III. Specific Functional Pharmacologic and Biologic Activity of Relaxin

The inventor believes that the necessary pharmacologic and/or functional biological activity of relaxin on the tissues of the body for treating the symptoms of involuntary muscle dysfunction and related conditions as claimed herein is established by the references already cited herein and further including the following references: MacLennan A. H., et al., *Ripening of the Human Cervix and Induction of Labor with Intracervical Purified Porcine Relaxin*, Obstetrics & Gynecology (1986) Vol. 68, No. 5, pp. 598–601; Poisner A. M., et al., *Relaxin Stimulates the Synthesis and Release of Prorenin From Human Decidual Cells: Evidence For Autocrine/Paracrine Regulation*, J of Clinical, Endocrinology an Metabolism (1990) Vol. 70, No. 6, pp 1765–1767; O'Day-Bowman M B, et al., *Hormonal Control of the Cervix in Pregnant Gilts. III. Relaxins's Influence on Cervical Hiochemical Properties in Ovariectomozed Hormone-Treated Pregnant Gilts*, Endocrinology (1991) Vol. 129, No. 4, pp. 1967–1976; Saugstad L F, *Persistent Pelvic Pain and Pelvic Joint Instability*, Euro Journal of Obstetrics & Gynecology and Reproductive Biology (1991) 41, 197–201; Bullesbach E E, et al., *The Receptor-Binding Sites of Human Relaxin II*, The Journal of Biological Chemistry (1992) Vol. 267, No. 32, pp. 22957–22960; Hall J. A., et al., *Influence of Ovarian Steroids on Relaxin-Induced Uterine Growth in Ovariectomized Gilts*, Endocrinology (1992) Vol. 130, No. 6, 3159–3166; Kibblewhite D., et al., *The Effect of Relaxin on Tissue Expansion*, Arch Otolaryngol Head Neck Surg. (1992) Vol. 118, pp. 153–156; Lee A B, et al., *Monoclonal Antibodies Specific for Rat Relaxin. VI. Passive Immunization with Monoclonal Antibodies Throughout the Second Half of Pregnancy Disrupts Histological Changes Associated with Cervical Softening at Parturition in Rats*, Endocrinology (1992) Vol. 130, No. 4, pp. 2386–2391; Bell R J, et al., *A Randomized, Double-Blind Placebo-Controlled Trial of the Safety of Vaginal Recombinant Human Relaxin for Cervical Ripening*, Obstetrics & Gynecology (1993) vol. 82, No. 3, PP. 328–333; Bryant-Greenwood G D, et al., *Sequential Appearance of Relaxin, Prolactin and IGFBP-1 During Growth and Differentiation of the Human Endometrium*, Molecular and Cellular Endocrinology (1993) 95, pp. 23–29; Chen S A, et al., *The Pharmacokinetics of Recombinant Human Relaxin in Nonpregnant Women After Intravenous, Intravaginal, and Intracervical Administration*, Pharmaceutical Research (1993) Vol. 10, No. 6, pp 834–838; Huang C., et al., *Stimulation of Collagen Secretion by Relaxin and Effect of Oestrogen on Relaxin Binding in Uterine Cervical Cells of Pigs*, Journal of Reproduction and Fertility (1993) 98, 153–158; Saxena P R, et al., *Is the Relaxin System a Target for Drug Development? Cardiac Effects of Relaxin*, TiPS (June 1993) Vol. 14, pp. 231, letter; Winn R J, et al., *Hormonal Control of the Cervix in Pregnant Gilts. IV. Relaxin Promotes Changes in the Histological Characteristics of the Cervix that are Associated with Cervical Softening During Late Pregnancy in Gilts*, Endocrinology (193) Vol. 133, No. 1, pp. 121–128; Colon J M, et al., *Relaxin Secretion into Human Semen is Independent of Gonadotropin Stimulation*, Biology of Reproduction (1994) 50, pp. 187–192; Golub M S, et al., *Effect of Short-Term Infusion of Recombinant Human Relaxin on Blood Pressure in the Late-Pregnant Rhesus Macaque (Macaca Mulatta)*, Obstetrics & Gynecology (January 1994) Vol. 83, No. 1, pp. 85–88; Jauniaux E., et al., *The Role of Relaxin in the Development of the Uteroplacental Circulation in Early Pregnancy*, Obstetrics & Gynecology (1994) 84(3): 338–342; Johnson M R, et al., *The Regulation of Plasma Relaxin Levels During Human Pregnancy*, Journal of Endocrinology (1994) 142, 261–265; Lane B, et al., *Decidualization of Human Endometrial Stromal Cells in Vitro: Effects of Progestin and Relaxin on the Ultrastructure and Production of Decidual Secretory Protein*, Human Reproduction (1994) Vol. 9, No. 2, pp. 259–266; Lanzafame F, et al., *Pharmacological Stimulation of Sperm Motility*, Human Reproduction (1994) Vol. 9, No. 2, pp. 192–199; Petersen K L, et al., *Normal Serum Relaxin in Women with Disabling Pelvic Pain During Pregnancy*, Gynecol Obstet Invest (1994) 38: 21–23; Tashima L S, et al., *Human Relaxins in Normal Benign and Neoplastic Breast Tissue*, Journal of Molecular Endocrinology (1994) 12, 351–364; Winn R J, et al., *Individual and Combined Effects of Relaxin, Estrogen, and Progesterone in Ovaroective Gilts. I. Effects on the Growth, Softening, and Histological Properties of the Cervix*, Endocrinology (1994) Vol. 135, No. 3, pp. 1241–1249; Winn R J, et al., *Individual and Combined Effects of Relaxin, Estrogen, and Progesterone on Ovariectomized Gilts. II. Effects on Mammary Development*, Endocrinology (1994) Vol. 135, No. 3, pp. 1250–1255; Bryant-Greenwood G D, et al., *Human Relaxins: Chemistry and Biology*, Endocrine Reviews (1994) 15: 1; p5–26; Johnson M R, et al., *Relationship Between Ovarian Steroids, Gonadotrophins and Relaxin During the Menstrual Cycle*, Acta Endocrinilogica (1993) 129: 121–5.

In addition, as known to those skilled in the art, relaxin's biologic/pharmacologic functional activity is further documented in other journal articles such as: (1) *Relaxin: A Pleiotropic Hormone*, Bani D, Gen. Pharmacol; 28(i): 13–22 (January 1997); (2) *Identification of Specific Relaxin-Binding Cells in the Cervix, Mammary Glands, Nipples, Small Intestines, and Skin of Pregnant Pigs*, Min G, Sherwood O D, Biol. Reprod., 55, 1243–52, December 1996; and (3) *Identification of Specific Relaxin-Binding Cells in the Human Female*, Kohsaka, et al., Biol. Reprod. 59, 991–999, 1998, all of which are hereby incorporated by reference.

IV. Production, Administration and Dosing of Relaxin

One method of administering relaxin within the body includes transplanting relaxin bearing cells from an ovary of a woman into the patient to be treated. In particular, ovaries can be harvested from a woman receiving an oophorectomy and the relaxin bearing cells can then be isolated and cell cultured into a large volume. After tissue matching these cells to a host, the cells are transplanted into the host body. Cells from normal women undergoing surgery for removal of ovaries will be used for themselves and also tissue matched for other matched hosts.

Fetal cells from both humans and animals can also be used as sources for relaxin or relaxin bearing cells. For example, see Bigazzi, U.S. Pat. No. 4,267,101. In addition, fetal cell transplants from animals to humans is known for treating a condition in the human with cells from an animal that are rich in a particular compound. For example, in a 1998 annual meeting of the American Epilepsy Society in San Diego Calif., Harvard researchers reported a successful transplant of brain cells from a pig fetus into the brain of a man with life-long untreatable seizures. The transplant reduced the number of seizures by 40 percent since the fetal pig nerve cells include a neurochemical, gamma-aminbutyric acid (GABA) that reduces seizures. The fetal pig cells were transplanted by placing a few drops of the fetal pig cells on the patient's brain.

To treat Alzheimer's, relaxin bearing cells may be directly transplanted into the brain through a bore hole in the skull, or alternatively by injecting the cells into the intrathecal space in the spine through a spinal tap. As another alternative, relaxin-bearing cells may be injected directly into the veins, allowing the cells to lodge in the lung tissues thereby permitting relaxin to be secreted to the rest of the body. This method would be similar to known methods of islet cell transplantation, as explained below. For Alzheimer's, transplantation by skull or intrathecal delivery are preferred while other transplant methods are appropriate for treating other relaxin-related maladies.

It is known to transplant insulin-producing cells (islets of Langerhans) from the pancreas to treat Type-I diabetes. In the newest form of this transplant, a diabetic patient was infused with islet cells (insulin producing cells) at University of Miami Diabetes Research Institute. After the infusion of the islet cells, the injected cells are carried by the bloodstream into the liver where the cells lodge and start secreting insulin in response to blood glucose levels. The cells are incorporated into an anatomical form by new capillaries growing around the lodged cells. Given relaxin's structural similarities to insulin, a similar cell transplant also would be effective and easier since the body's demand for relaxin is not as cyclical as insulin.

Relaxin and its analogs can be formulated using known methods to prepare pharmaceutically useful compositions by combining relaxin with a pharmaceutically acceptable carrier. The following references provide an example of known methods of administration and dosing of relaxin: U.S. Pat. Nos. 4,835,251; 5,451,572; 5,811,395; 5,811,388; 5,166,191; 5,753,623; and 5,656,592.

Of course the dose for treating aging symptoms and neurodegenerative symptoms depends on several factors including the route of administration, formulation method, patient age and medical history, and the overall administration schedule to be employed. Potential administration routes for relaxin include: parenteral, subcutaneous, intraperitoneal, intravenous, intramuscular, transdermal, transnasal, oral, transbronchial, topical.

It also may be desirable or necessary to couple administration of relaxin with estrogen, progesterone, and/or testosterone to achieve the desired synthesis and elevation of relaxin in the blood stream.

All references cited herein are expressly incorporated by reference.

Although the present invention has been described with reference to preferred embodiments, workers skilled in the art will recognize that changes may be made in form and detail without departing from the spirit and scope of the invention.

What is claimed is:

1. A method of treating osteodegenerative joint dysfunction by concomitantly administering to a patient exhibiting joint pain and inflammation from osteodegenerative dysfunction of a therapeutically effective amount of:
   (1) relaxin hormone; and
   (2) glusocamine sulfate.

2. A method of treating Alzheimer's by concomitantly administering to a patient exhibiting memory loss from Alzheimer's of a therapeutically effective amount of:
   (1) relaxin hormone; and
   (2) estrogen.

* * * * *